United States Patent [19]
Belyavsky et al.

[11] Patent Number: 5,814,445
[45] Date of Patent: Sep. 29, 1998

[54] METHOD OF IDENTIFICATION AND CLONING DIFFERENTIALLY EXPRESSED MESSENGER RNAS

[75] Inventors: Alexander V. Belyavsky; Natalia B. Ivanova, both of Moscow, Russian Federation

[73] Assignee: New York Blood Center, New York, N.Y.

[21] Appl. No.: 499,899

[22] Filed: Jul. 11, 1995

[30] Foreign Application Priority Data

Jul. 11, 1994 [RU] Russian Federation ............. 94024056

[51] Int. Cl.⁶ .............................. C12Q 1/68; C12P 19/34; C07H 21/04
[52] U.S. Cl. .......................... 435/6; 435/91.2; 435/91.5; 435/91.51; 536/24.33; 935/8; 935/18; 935/77; 935/78
[58] Field of Search ............................. 435/6, 91.1, 91.2, 435/91.3, 91.5, 91.51; 536/24.33; 935/8, 77, 78, 18

[56] References Cited

U.S. PATENT DOCUMENTS

| | | | |
|---|---|---|---|
| 5,459,037 | 10/1995 | Sutcliffe et al. | 435/6 |
| 5,599,672 | 2/1997 | Liang et al. | 435/6 |
| 5,599,696 | 2/1997 | Mueller | 435/91.2 |

OTHER PUBLICATIONS

Youn. Hoitto Lee and Victor D. Vacquier "Reusable cDNA libraries coupled to magnetic beads" Analytical Biochemistry 206:206–207 1992.

Minoru S.H. Ko "An equalized cDNA library'by the reassociation on shor dscDNA "Nucleic Acids Research 18(19):5705–5711 Oct 11, 1990.

R. DeWachter et al. "Two–dimensional gel electrophoresls of nucleic acids "in Gel Electrophonesis of Nucleic Acids: A Practical Approach. ed. D. Rickwood & B.D. Hames IRI Press at Oxford University Press New York 1990 pp. 182–200 edited by Ausubel et. al. "Short Protocols in Molecular Biology ".
John Wiley & Sons, New York (1989) pp. 75–76.
Promega 1992–1993 catalog pp. 164–165 and 183.
Clontechniques Jan. 1993 vol. VIII, No. pp. 1–3.
Ausubel eds. Short Protocols in Molecular Biology (1989) John Wiley & Sons. New York pp. 75–76 & 132–133.
Promega Protocols & Applications guide (1991) pp. 17–43.

*Primary Examiner*—W. Gary Jones
*Assistant Examiner*—Debra Shoemaker
*Attorney, Agent, or Firm*—Hoffmann & Baron, LLP

[57] ABSTRACT

A method of identification of differentially expressed messenger RNA (mRNA) which consists of synthesizing from a set of sequences of mRNA sets of fragments of complementary DNA (cDNA), which are separated with the aid of gel electrophoresis and the pictures of separation of the cDNA from different types of cells are compared and fragments with the aid of restriction nucleases. A method of cloning of differentially expressed mRNAs consists of synthesizing from sets of sequences of MRNAs from different types of cells sets of fragments of complementary DNA (cDNA) which are separated with the aid of gel electrophoresis, the pictures of the separation of the cDNA from different types of cells are compared, fragments of cDNA with different signal intensities are separated from the gel, amplified with the aid of a polymerase chain reaction and clones to a plasmid or phage vector. For the formation of the set of fragments one carries out cleavage of the cDNA with the aid of restriction endonucleases and uses only those fragments of cDNA that correspond to the 3' or 5' end regions of the mRNAs.

41 Claims, 6 Drawing Sheets

METHOD OF IDENTIFICATION AND CLONING DIFFERENTIALLY EXPRESSED MESSENGER RNAS

ART

This invention relates to the field of molecular biology and can be used in medicine and molecular biology for analysis of gene expression and diagnosis and identification of mechanisms of pathology at the genetic level.

PRIOR ART

Differential expression of genes, which is realized via the synthesis of various sets of messenger RNAs (mRNAs), is the basis of the variety of phenotypes and functions of the cells of living organisms. In this connection one can understand the importance of methods that might allow identification and investigation of differentially expressed mRNAs, i.e., those RNAs, whose concentration in the cellular mRNA pool differs in two or more types of cells or changes in dependence on the functional state of the cells.

A number of methods have been described for the detection and cloning of differentially expressed mRNAs. In most cases they come down to the use of the method of hybridization of nucleic acids. In the differential screening method (see literature [1]) by means of transfer to nitrocellulose or nylon filters replicas of libraries of complementary DNA (cDNA) from the population of cells A sown in dishes are hybridized alternately with labeled preparations of cDNA from the population of cells A, B, C and so forth. Since the hybridization signal obtained from individual clones theoretically should be proportional to the representation of the corresponding cloned sequence in the cDNA preparation, one can, from the level of the signal obtained from different preparations, identify clones corresponding to genes that are expressed differentially in the populations of cells A, B and so forth. An important shortcoming of this approach is its low sensitivity, since only highly represented sequences (as a rule, those comprising at least 0.1% mRNA) can be detected. For less common sequences the hybridization signal does not exceed the background. In addition, in this approach one can examine only a small number (from several thousands to several tens of thousands) of clones. Another shortcoming is that information about the individuality of the clone (the description of its location in the dish or replica) is lost at the end of work with these replicas and cannot be used in subsequent experiments. Moreover, cDNA libraries from different types of cells are not comparable in that identical sequences occupy different places on filters in different libraries. Thus, conversion from one type of cells to other types is essentially impossible. Recently attempts have been made to create ordered cDNA libraries containing individual clones distributed in the cells of 96-well planchets. However, this does not eliminate the principal shortcoming of low sensitivity. In addition, sets of clones obtained from one type of cell are still not comparable to sets of clones from another type of cell.

The method of subtracted hybridization is used in order to overcome the low sensitivity of the differential screening method [1]; in this method a cDNA preparation from cells A is hybridized with a cDNA or mRNA preparation from cells B, after which the resulting hybrids are removed by one or another method. The resulting preparation is rich in sequences that are specific for preparation A. This "subtracted" preparation can be used both for the creation of libraries and for differential screening, since it makes it possible both to increase the probability of finding differentially expressed sequences and to increase the sensitivity of detection of poorly represented sequences. However, the use of this procedure makes the approach lengthy and laborious and, in addition, the gain in sensitivity is still insufficient for detection of rare sequences and is accompanied by the loss of the possibility of making a direct comparison of the level of gene expression in different cells.

Recently a modification of the differential screening method was proposed, in which instead of cloned sequences large orderly arranged sets of oligonucleotides are used for immobilization on a solid substrate, for example, all possible tetradecanenucleotides containing the common sequence AATAAA, which is encountered in most mRNAs [2]. This method theoretically provides an exhaustive search of a much larger set of mRNA sequences than in standard differential screening. The shortcoming of this approach, like other differential screening methods, is that under conditions of hybridization with an excessively complex mixture of cDNA molecules, the frequencies of representation of which may vary by factors of hundreds and thousands, the probability of the appearance of false signals owing to cross hybridization becomes significant, which makes reliable detection and quantitative analysis of rare mRNA sequences problematical. An additional problem is the need for synthesis and immobilization on a small area of from several dozens to hundreds of thousands of oligonucleotides,. which requires a large initial investment. In addition, the approach in and of itself does not provide the possibility of cloning any long segments of differentially expressed mRNAs, which requires a separate operation.

Closest to the present invention is a method which is called "PCR mated with reverse transcription, with arbitrary primers" (arbitrary primed RT-PCR). In this method cDNA synthesized by mRNA is used to create a set of cDNA fragments of discrete length with the aid of a polymerase chain reaction (PCR) using primers of a random sequence under nonrigorous conditions which contribute to priming and amplification not of one, as is usual in standard PCR, but rather of a whole group of cDNA sequences. The set of discrete cDNA fragments is separated by electrophoresis in acrylamide gel and compared with a set of fragments obtained under identical conditions from a different type of cell. By using many arbitrary primers, one can compare one or several discrete cDNA fragments to most mRNA species. Two principal modifications of this approach have been proposed. One of them uses one or two "arbitrary" primers [3,4]. The second approach uses one arbitrary and one oligo(dT) primer that contains two additional bases at the 3' end [5,6,7]. In this case the amplified segments are adjacent to the 3' end (poly(A) tail) of the mRNA. An important shortcoming of this approach is the fact that no more than a few dozen sequences are amplified in a single reaction. Thus, for an exhaustive search of 10–15 thousand RNA sequences expressed in individual types of cells or tissues, as a minimum several hundred (probably several thousand) reactions must be carried out. In addition, the sampling of sequences amplified in one reaction is random and, therefore, in the exhaustive search of a significant portion of sequences of cellular mRNA there will be a very significant accumulation of excess information. Thus, after a survey of 50% of all sequences, in each subsequent reaction only ½ of the amplified sequences will be new. At a depth of review of 90% the fraction of new sequences will fall to ¹⁄₁₀. Probably the most significant shortcoming of the approach is its poor reproducibility, which is connected with the fact that under weakly selective priming conditions small variations in the starting conditions or the quality of the RNA preparations, primers and other parameters will cause significant quantitative changes in the spectrum of amplified cDNA fragments. Thus, if the optimum annealing temperature is 42° C. a shift of the annealing temperature up or down by 2° resulted in the appearance of a substantial background (i.e., additional bands) or to disappearance of some bands [7]. Second, according to the data of the authors of [7] when parallel experiments were carried out, about 95% of bands proved to be reproducible [6]. Thus, the level of nonreproducibility (5%) is comparable to or even exceeds the level of differences between mRNA populations. According to our data, when this approach is used, the number of reproducible differential bands is usually smaller than the number of nonreproducible bands. It is probable that the sensitivity of the approach to the quality of preparations of RNA, primers, annealing time and other parameters may substantially prevent a comparison of results with known data.

SUMMARY OF THE INVENTION

The basis of the invention was the task of supporting the possibility of a direct qualitative and quantitative comparison of the spectra of mRNAs synthesized in different types of cells of the same organism, the possibility of detection of differentially expressed RNAS, including those with a low level of representation, the possibility of correlating these RNAs with known ones, and also the possibility of cloning fragments of such RNAs. The problem is resolved by the fact that the set of messenger RNAs expressed in a cell by means of synthesis of complementary DNA (cDNA) with subsequent fragmentation of the cDNA by frequently cleaving restriction endonucleases (having four- or five-letter recognition sites) and use of the cDNA fragments corresponding to the 3' or 5' ends of the mRNA, is represented in the form of a set of fragments of cDNA of discrete length, no more than one fragment for each species of mRNA, and at least one of the ends of the fragments carries the marker or group necessary for detection. The generated fragments of cDNA originate from the 3' end (adjacent to the poly(A) tail) or 5' end regions of the mRNAs and support representation, depending on the specific embodiment of the invention, of from 90% to essentially 100% of mRNA sequences. For an increase of the sensitivity of the approach and for unambiguous identification of individual fragments the set of cDNA fragments may be divided into several nonintersecting subsets of fragments. The sets or subsets are divided by one- or two-dimensional gel electrophoresis and detection of the marker and comparison of the separation pictures is carried out. In this case the intensity of the signal from each fragment of cDNA varies for mRNA preparations from different cells in proportion to the representation of the sequence corresponding to it in the mRNA pool. If necessary in the detection stage, by means of transfer of the separated fragments to a membrane and sequential hybridization with a set of oligonucleotides, which partially overlap the common end sequence of the fragments, additional analysis of the separation picture is possible. The separated cDNA fragments, after additional operations can be amplified and investigated by means of restriction and hybridization analysis and also sequencing, and can be cloned to a plasmid or phage vector.

Thus, in the proposed invention, in contrast to the approach using arbitrary primers, at least one of the boundaries of the fragments is specified by the position of the restriction site*; in addition, in the proposed approach a set of cDNA fragments that is as representative as possible is created at first and then divided into nonintersecting subsets and then separated with the aid of gel electrophoresis. The use of the reaction of cleavage of DNA by restriction nucleases, which is characterized by high specificity, completeness of cleavage and low sensitivity to variations of temperature conditions, makes it possible to make the approach much more reproducible and, therefore, will make possible a reliable comparison with independently conducted experiments. These characteristics, together with the high resolution of the method, will make it possible to begin the creation of databases of gel coordinates of expressed sequences. The proposed method makes it possible to eliminate the excess of information that is characteristic for the method with arbitrary primers. In addition the presence of one common population of cDNA fragments in the initial stages makes it possible to conduct such operations as frequency equalizations by means of self-hybridization of the population of cDNA fragments [8], which will make it possible to reduce substantially the level of representation of the most frequently encountered mRNA species and will help the isolation of very rare mRNA sequences owing to a reduction of interference from frequently encountered sequences.

DETAILED DESCRIPTION OF THE INVENTION

Figure 1:
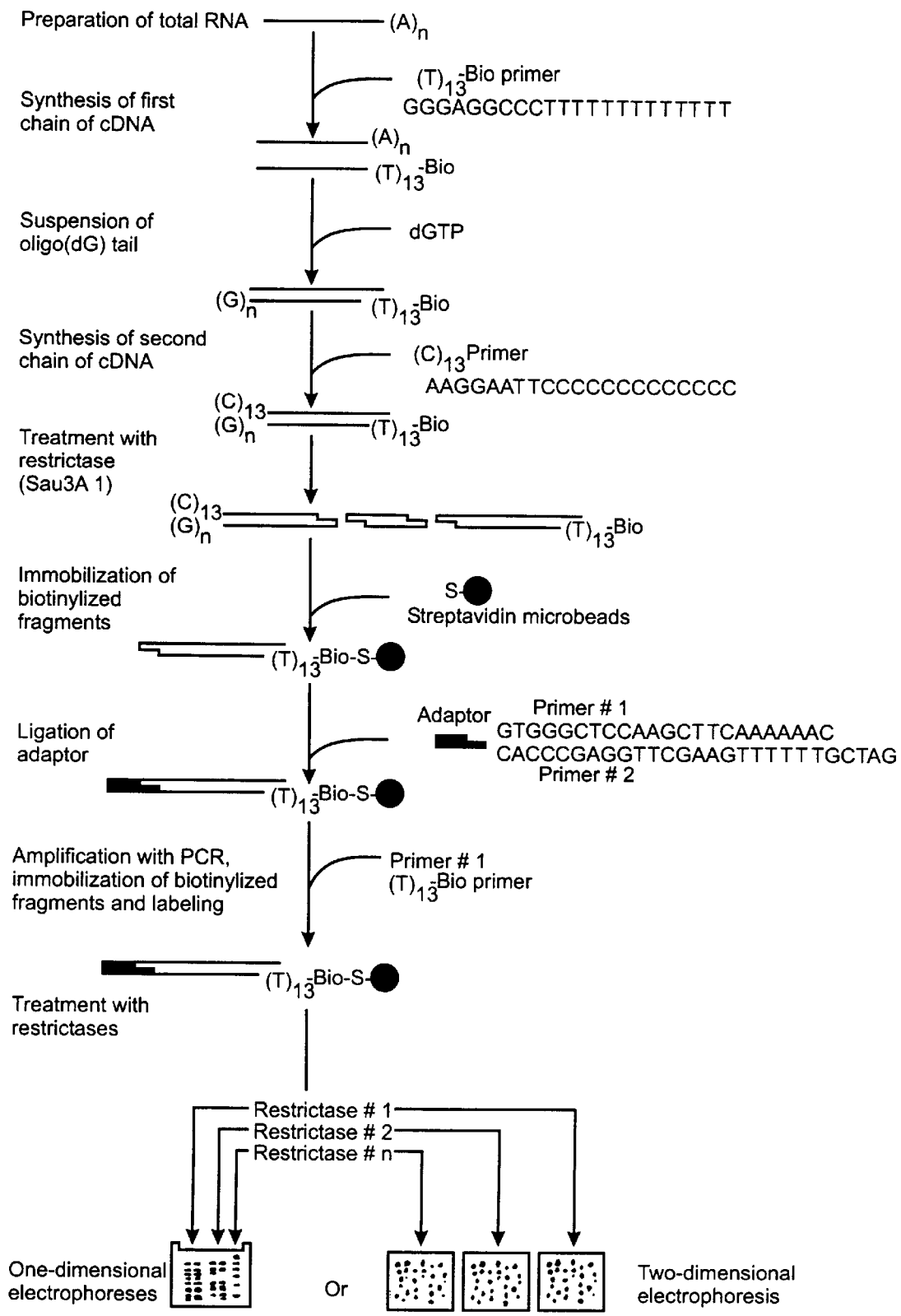
FIG. 1 shows one version of implementing the invention by means of the formation of a set of 3' end labeled fragments of cDNA, dividing it into subsets of fragments with the aid of immobilization on a solid support and sequential treatment with a series of restriction nucleases, and separation of the resulting subsets by electrophoresis.

One variation of the announced method is presented in more detail below.

Synthesis of the first chain of cDNA is accomplished by the enzymatic route with the aid of reverse transcriptase and oligo(dT) primer immobilized on microgranular solid support or of oligo(dT)-containing primer carrying a biotin group at the 5' end. For synthesis of the second chain of cDNA, preliminary suspension of the oligo(dG) tail at the 3' end of the first chain of cDNA with the aid of terminal transferase is carried out. Synthesis of the second chain is carried out with modified DNA polymerase of phage T7 sequenase (United States Biochemicals, USA) using an oligo(dC)-containing primer as primer. Complete hydrolysis of the cDNA with restriction endonuclease having a four-letter recognition site (for example, Sau3A), rinsing of the released cleavage products and ligation of the adaptor complementary to the cleavage site are carried out. If a biotinylized primer is used for synthesis of the first chain, the cDNA before or after cleavage with restrictase is bonded to a streptavidin-containing solid support (Streptavidin MagneSphere, Promega, USA). The ability of streptavidin to bind the biotin group rapidly and stably is used in this operation. To increase the above material, amplification of the fragments of cDNA is carried out by means of PCR using the primer that is in the adaptor and modified oligo(dT) primer containing the biotin group at the 5' end. After immobilization of the fragments in the streptavidin-containing solid support the free ends are removed by treating with 100 mM NaOH, and then the primer is annealed in the immobilized chains, the label is added to the 3' end of the primer by the chain lengthening reaction with DNA polymerase using radioactive $\alpha$-$^{32}$P DATP or $\alpha$-$^{33}$P DATP, after which unlabeled deoxynucleotide triphosphates are added and complete chains of cDNA are completed. The sequence of primer and segment cDNA annealed with it and also the conditions of the labeling reaction are such that the region labeled is limited to the adaptor sequence. After adding the marker, sequential exhaustive cleavage with 8–10 restrictases is carried out, with restrictases having 6-letter recognition sites being used first, followed by 5-letter and finally 4-letter recognition sites. The released labeled fragments of cDNA after each reaction are collected separately. Separation of the fragments is done with one of the systems for electrophoresis in polyacrylamide or similar gel (Hydrolink, AT Biochem, USA). The system of two-dimensional electrophoresis of DNA, in which separation of the double-chain DNA along the length is carried out in the first reaction, and separation with regard to composition is done in the second direction (more precisely, over the melting profile) with a denaturing gradient [9]. According to literature data, even after transfer to a membrane, which significantly degrades resolution, this kind of system makes it possible to separate at least 625 fragments of DNA on one gel [10]. To all appearances the upper limit of resolution is 1 to 1.5 thousand DNA fragments. If the population of cDNA fragments is divided into 8–12 nonintersecting sets, one can separate up to 10–15 thousand fragments, i.e., essentially all mRNAs expressed in cells of a single type. The signal from the separated fragments is detected by means of autoradiography on x-ray film. The pictures obtained from preparations of RNA from different types of cells are compared with each other, the correspondence between individual fragments of cDNA from different cells is established from the position in one- or two-dimensional electrophoresis and fragments giving a differential signal are identified.

In order to ascertain the sequence of known sequences to which one or another spot on the two-dimensional electrophoreogram may correspond, one first, based on cloned sequences of mRNAs in the data bank, determines which sequences may give fragments of the corresponding link and then, by using the algorithm for prediction of mobilities of fragments of DNA in a denaturing gradient [11], one can choose from these sequences the one whose melting profile most accurately corresponds to the position occupied by the fragment in the second direction.

Figure 2:
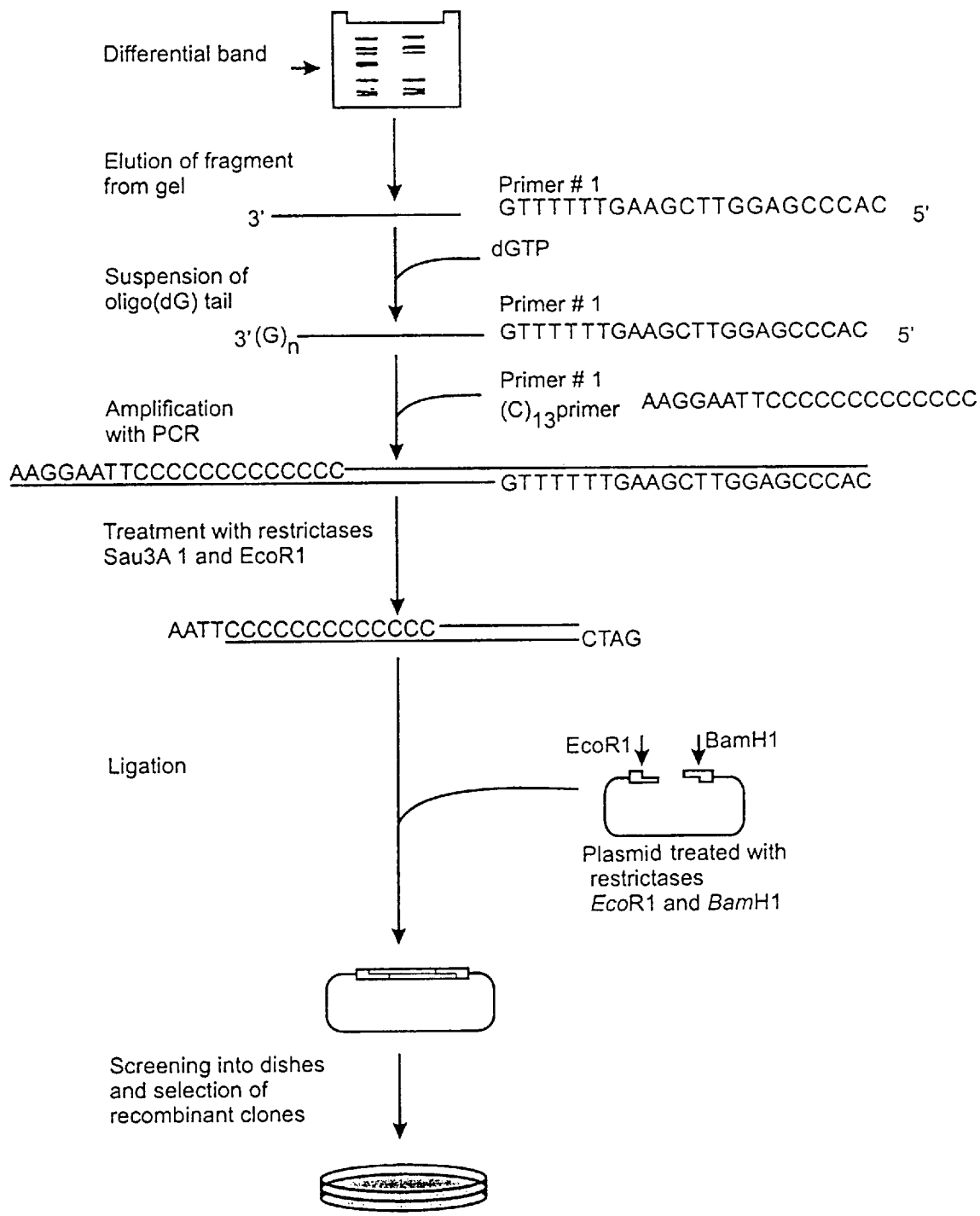
FIG. 2 shows a scheme of amplification and cloning of cDNA fragments obtained and separated in gel with the aid of the method shown in FIG. 1.

In order to obtain the needed fragment in a quantity sufficient for analysis and cloning, the fragment is eluted from the gel, the oligo(dG) tail is suspended with the aid of terminal transferase, and then amplified by means of PCR using adaptor primer and oligo(dC) (FIG. 2). The identical nature of the fragment of the known sequence can be verified by means of restriction analysis or by determining the nucleotide sequence directly in the amplified fragment. In addition, the amplified fragment may be easily cloned to the plasmid or phage vector.

Our computer analysis of 659 cloned sequences of mouse mRNA having a sequestered region belonging to the poly(A) tail showed that when the restriction endonuclease Sau3A (recognition site: GATC) was used for cleavage of the cDNA 93% of all mRNAs will be cleaved by the enzyme and, therefore, will participate in the analysis. The fraction of sequences of mRNAs participating in the analysis can be increased to 99%–99.5%, if cleavage is done with a second restrictase having a different recognition site of those sequences of cDNA that were not cleaved by the first restrictase. The computer analysis also shows that second cleavage of immobilized fragments of cDNA with a set of restriction endonucleases can reach the overwhelming majority of fragments (96% if ten four-letter restrictases are used). Thus, from 90 to 96% of all mRNA sequences of the cell will be represented in the form of discrete fragments of cDNAs and will participate in the analysis period.

The proposed method has high sensitivity. Using only 1 $\mu$g of cDNA fragments for labeling it is easy to obtain inclusion to $10^8$ count/min. This level of labeling makes it possible to detect mRNA sequences that make up from 0.001% to 0.0001% of the mRNAs of the cell.

Figure 6:
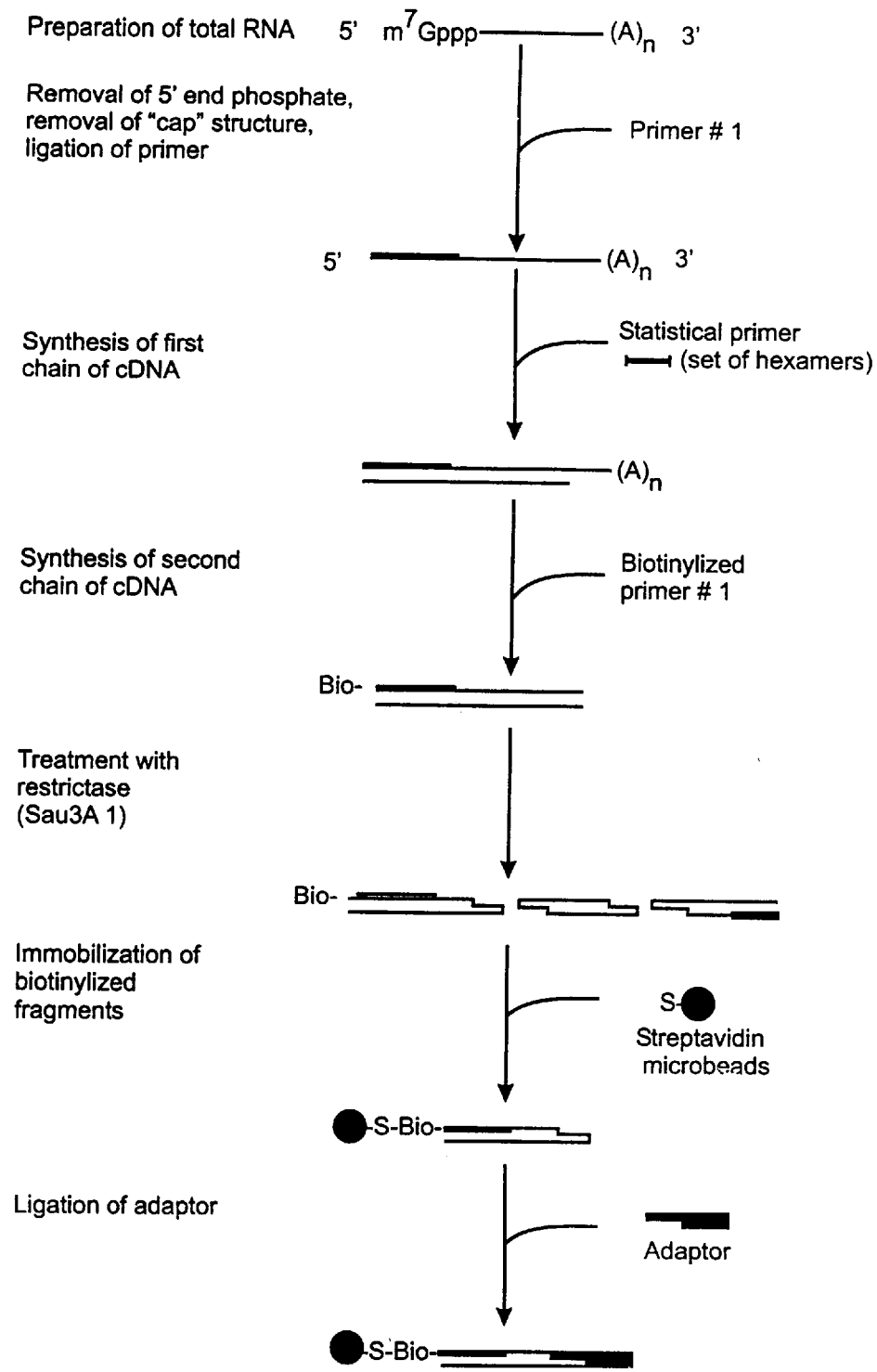
FIG. 6 shows a method of creating a set of 5' end fragments of cDNA.

Besides the variation described above, there are also other variations of the invention. Synthesis of the second chain of cDNA can be accomplished by other known methods by using as primers for synthesis the chain of RNA in hybrid cDNA-RNA that has been cleaved with the aid of RNAse H or by using self-priming of the first cDNA chain after hydrolysis of the RNA chain [12]). The most important modification is the use of the alternative method of dividing the set of 3' end fragments of cDNA into nonintersecting subsets of fragments by means of amplification with the aid of 12 different pairs of primers, which include a) four versions of a modified adaptor primer, which includes an adaptor end sequence that is common for all fragments of cDNA and that each contains one additional base at the 3' end; b) three versions of oligo(dT)-containing primer that contains one additional base at the 3' end. In this case one employs the property of Taq DNA polymerase to extend only those primers that contain a completely paired 3' end base [13]. In this version it is not necessary to carry out second cleavage with the set of restrictases and, therefore, the share of mRNA sequences that participate in the analysis can essentially reach 100%. one further important version of the approach is creation of a set of fragments of cDNAs corresponding to the 5' end of the mRNAs (FIG. 6). For this one uses specific labeling of the 5' end of the mRNAs with an oligonucleotide primer (primer 1) in accordance with the procedure of [14]. After this, one synthesizes the first chain with the aid of a set of random hexamer primers, synthesizes the second chain with the aid of primer 1 containing a biotin group at the 5' end, immobilizes the cDNAs in streptavidin microgranules, followed by hydrolysis of the cDNAs with restrictase, ligation of the adaptor and other procedures, as indicated above. Dividing the set of 5' end fragments of cDNAs into subsets is accomplished either by immobilization of the labeled fragments and sequences by treatment with restrictases or with the aid of separate reactions of amplifications with end primers that contain an additional base at the 3' end, as indicated above.

Besides two-dimensional electrophoresis using a denaturing gradient in the second direction, it is also possible to use systems of two-dimensional electrophoresis that use in the second direction separation of single-chain DNA under nondenaturing conditions owing its conformational polymorphism [15] or cleavage of DNA after the first direction by frequently cleaving restrictases [16] and separation by length in the second direction.

Besides the use of radioactive $^{32}P$ or $^{33}P$ markers with subsequent autoradiography for detection, a nonradioactive variation of detection may also be accomplished; in this version labeling of the fragments of cDNA is done with biotin groups or other chemical groups that after transfer of the fragments to the membrane and immobilization are detected with one of the commercial systems of nonradioactive detection using chemiluminescence.

Detection of the separated unlabeled elements of cDNA can be done by transfer of fragments to a membrane and hybridization with a labeled adaptor primer. In this case, after hybridization with the adaptor primers that contain additional bases at the 3' end, selected visualization of the subsets of fragments separated in the given gel is possible.

INFORMATION CONFIRMING THE POSSIBILITY OF IMPLEMENTATION OF THE INVENTION

To support the possibility of identification and cloning of differentially expressed mRNAs, the experiments presented in the following example were carried out.

EXAMPLE

Identification and cloning of mRNAs differentially expressed in mouse thymus and spleen.

Preparations of total RNA are extracted from mouse thymus and spleen in parallel using extraction with acid phenol [17]. Synthesis of the first cDNA chain was accomplished under the following conditions: 37° C., 60 min, reaction volume 20 µL, 5 µg total RNA, 200 U reverse transcriptase Superscript (Gibco-BRL, USA), 10 pmol (T)-primer, biotinylized at the 5' end (sequence 5' -biotin-GGGAGGCCC(T)$_{13}$) (SEQ ID NO: 1), 30 U RNAse inhibitor from human placenta, DATP, dGTP, dCTP, dTTP (1 mM each), 1× buffer of reverse transcriptase in accordance with manufacturer's recommendations make up the reaction mixture. Removal of the primer is done with the aid of reprecipitation using cetyltrimethylammonium bromide [18], after which additional purification is carried out on a Wizard column (Promega, USA) according to manufacturer's recommendations. The purified preparation is precipitated with 3 volumes of ethanol using 2 µg glycogen (Boehringer-Mannheim, Germany) as carrier.

Suspension of the oligo(dG) tail is done under the following conditions: 37° C., 20 min, reaction volume 20 µL, with the reaction mixture containing hybrid mRNA-first chain of cDNA, 20 U terminal transferase (Gibco-BRL, USA), 0.02 mM dGTP, 1× buffer of terminal transferase in accordance with manufacturer's recommendations. Synthesis of the second chain of cDNA is done under the following conditions: denaturation 98° C., 1.5 min, annealing 60° C., 2 min, elongation 72° C., 20 min, reaction volume 25 µL, reaction mixture contains: hybrid mRNA-cDNA, 10 pmol (C)-primer (sequence 5'-AAGGAATT(C)$_{13}$) (SEQ ID NO: 2), DATP, dGTP, dCTP, dTTP (0.1 mM each), 1.5 U DNA polymerase Bio-Taq (Biomaster, Russia), 1× buffer of Bio-Taq in accordance with manufacturer's recommendations. Cleavage of cDNA by restriction endonuclease is done under the following conditions: 37° C., 60 min, reaction volume 20 µL, 4 U restriction endonuclease Sau3A (New England Biolabs, USA), 1× buffer of enzyme (according to manufacturer's recommendations). After hydrolysis the reaction is stopped by the addition of EDTA to 20 mM and the 3' end fragments of cDNA are immobilized on Streptavidin microbeads (Promega, USA) in accordance with manufacturer's recommendation. The adaptor is added:

1. 5'-GATCGTTTTTTGAAGCTTGGAGCCCAC-3' (SEQ ID NO: 3)
2. 3'-CAAAAAACTTCGAACCTCGGGTG-5' (SEQ ID NO: 4)

and ligated at 12° C. overnight. Reamplification of the cDNA fragments with the aid of PCR is done using Bio-(T$_{13}$) primer and primer 1 under the following conditions: denaturation 95° C., 1.2 min, annealing 55° C., 1.5 min, elongation 72° C., 3 min* reaction volume 100 µL, reaction mixtures contains: 30 pmol Bio-(T) primer, 30 pmol primer 1, 2.5 U DNA polymerase Bio-Taq; the mixture of deoxynucleotide triphosphates, 0.1 mM each, 1× buffer of Bio-Taq. After 15 PCR cycles the fragments are immobilized on Streptavidin microbeads (Promega, USA), then the free chain is removed by treatment with 100 mM NaOH for 10 min, rinsing with a buffer of composition: 40 mM Tris-Cl, pH 7.0, 20 mM MgCl$_2$, 50 [?] NaCl, primer 3 (5'-GTGGGCTCCAAGCTTC) (SEQ ID NO: 5) is annealed, radioactive α-$^{32}P$ dATP is added and the marker is added over 5 min using modified DNA polymerase of phage T7 Sequenase (United States Biochemicals, USA), after which the mixture of dNTP is added (to 0.2 mM each) and complete chains are finished. Cleavage of the fragments is done successively with restriction endonucleases EcoRV, PstI, MspI, Hin PI (New England Biolabs, USA). After each endonuclease treatment the fragments are collected, denatured and applied to sequestering polyacrylamide gel (5% acrylamide, 0.25% methylene-bisacrylamide, 7M urea, 1× TBE buffer). Separation of the fragments is done under standard conditions after which the gel is fixed in 10% acetic acid for 30 min, dried and autoradiographed. The sequences of mRNAs that are differentially expressed in thymus and spleen are identified by means of a direct comparison of the sets of bands of cDNA obtained from thymus and spleen and separated in adjacent tracks. For cloning of the differentially expressed sequences the corresponding bands of gel are cut apart and the fragments are eluted by incubation in 150 mM NaCl, 50 mM Tris-Cl, pH 8.0, 10 mM EDTA overnight. Then precipitation of the fragments is carried out with three volumes of 96% ethanol using glycogen as carrier. The oligo(dG) tail is suspended at the 3' end of the fragment using terminal transferase, as described above, and the fragment that has been processed in this way is amplified by means of PCR using (C) primer and primer 1.

The amplified fragment is purified with the aid of electrophoresis in agarose gel, transferred to low melting agarose and recovered in pure form with the aid of phenol extraction [19]. For cloning of the fragments they are treated with restrictase Sau3A and EcoRI and ligated to plasmid vector pUC18 cleaved by restrictase BamHI and EcoRI, after which they transform competent bacteria. The presence of recombinant clones is verified with the aid of amplification of insertions using PCR. Verification of the specificity of the cloned fragments is done by means of hybridization of $^{32}$P-labeled insertions from clones with blots of amplified cDNA and poly(A)$^+$ RNA from the corresponding organs.

Figure 3:
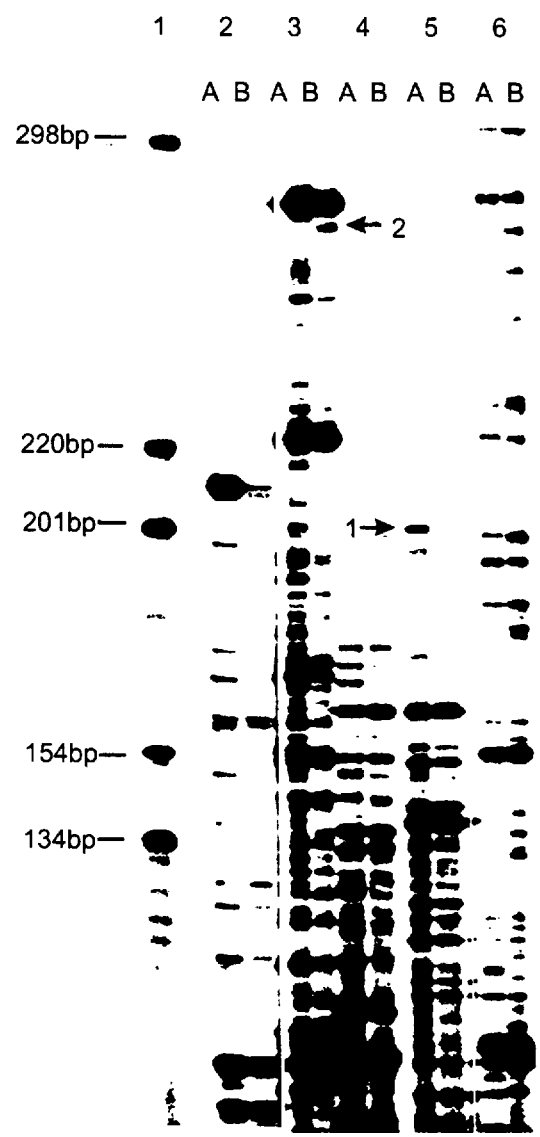
FIG. 3 shows a representation of separation in denaturing polyacrylamide gel electrophoresis of $^{32}$P-labeled fragments of cDNA from preparations of RNA of mouse thymus (a) and mouse spleen (b) obtained with the aid of the method presented in FIG. 1. The first cleavage was done with the enzymes Sau3A (2–5) and BamHI (6), the second with the enzymes EcoRV (2), PstI (3, 6), MspI (4) and Hin PI (5). Microfragments of DNA are plotted on the left (1) and their lengths in nucleotides are indicated.
Figure 4A:
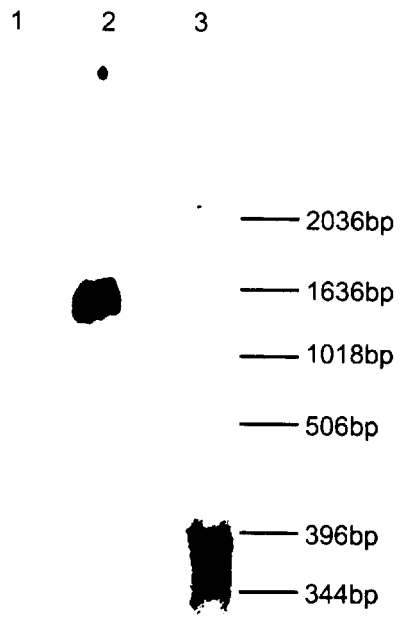
FIGS. 4(A) and 4(B) represent hybridization of cloned fragment 1(a) and fragment 2(b) with preparations of poly (A)$^+$ RNA from mouse spleen (1) and thymus (2) separated by electrophoresis and transferred to a membrane. The hybridization confirms the specificity of expression that follows from FIG. 3. On the right are plotted marker single-chain DNA fragments and their lengths and nucleotides are indicated.
Figure 4B:
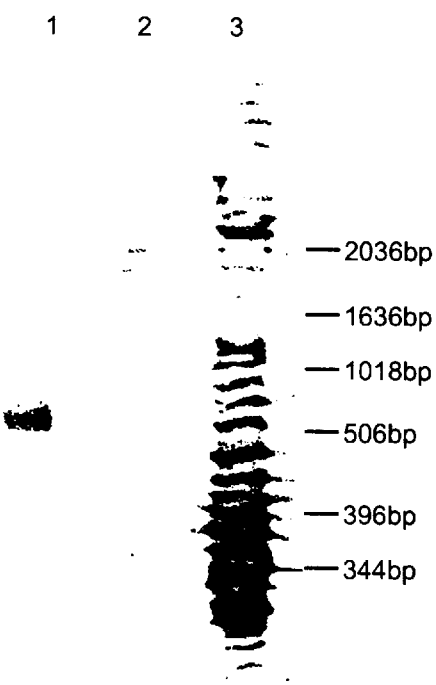
Figure 5:
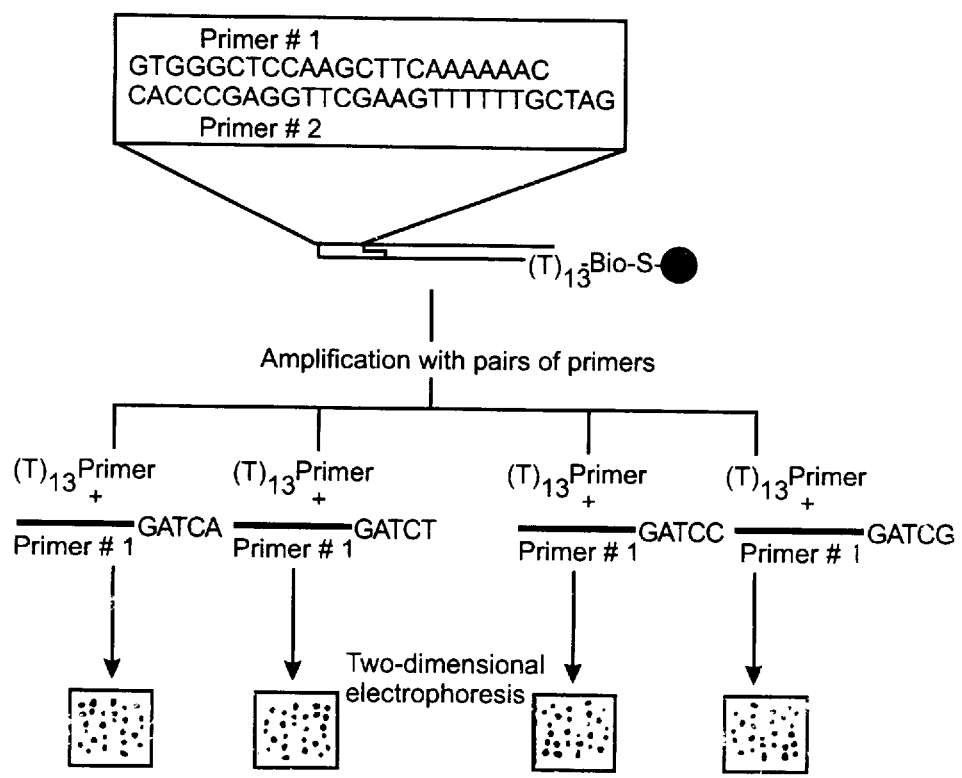
FIG. 5 shows an alternative method of dividing the set of 3' end fragments of cDNA obtained by the method shown in FIG. 1 into four subsets by means of amplification of the set of fragments by a polymerase chain reaction with adaptor primers that contain a supplemental base at the 3' end beyond the limits of the part that is common for all fragments.

The data in FIG. 3 show that this method leads to the formation of a multitude of labeled discrete fragments of cDNAs which can be separated in gel electrophoresis, and in comparing the pictures of the separation of cDNAs from two different organs one can identify differential bands. The fragments corresponding to the differential bands can be amplified and cloned by the method indicated in FIG. 2. The data given in FIG. 4 show that the cloned fragments of cDNAs are indeed mRNAs differentially expressed in two organs.

REFERENCES

1. Sargent, T. D. Isolation of differentially expressed genes. Methods in Enzymol. (1987) 152, 423–432.
2. PCT/GB 89/00460 (1989)
3. Welsh, J., Chada, K., Dalal, S. S., Cheng, R., Ralph, D., McClelland, M. Arbitrarily pried PCR fingerprinting of RNA. Nucl.Acids Res. (1992) 20, 4965–4970.
4. Ralph, D., McClelland, M., Welsh, J. RNA fingerprinting using arbitrarily primed PCR identifies differentially regulated RNAs in mink lung (Mv1Lu) cells growth arrested by transforming growth factor-beta 1. Proc.Natl.Acad.Sci.USA (1993) 90, 10710–10714.
5. Liang, P., Pardee, A. B. Differential display of eukaryotic messenger RNA by means of the polymerase chain reaction. Science (1992) 257, 967–971.
6. Liang, P., Averboukh, L., Pardee, A. B. Distribution and cloning of eukaryotic mRNAs by means of differential display: refinements and optimization. Nucl.Acids Res. (1993) 21.
7. Bauer, D., Muller, H., Reich, J., Riedel, H., Ahrenkiel, V., Warthoe, P., Strauss, M. Identification of differentially expressed mRNA species by an improved display technique (DDRT-PCR). Nucl.Acids Res. (1993) 21, 4272–4280.
8. Sasaki, Y. F., Iwasaki, T., Kobayashi, H., Tsuji, S., Ayusawa, D., Oishi, M. Construction of an equalized cDNA library from human brain by semi-solid self-hybridization system. DNA Research (1994) 1, 91–96.
9. Fischer, S. G., Lerman, L. S. Length-independent separation of DNA restriction fragments in two-dimensional gel-electrophoresis. Cell (1979) 16, 191–200.
10. Uitterlinden, A. G., Slagboom, P., Knook, D. L., Vijg, J. Two-dimensional DNA fingerprinting of human individuals. Proc.Natl.Acad.Sci.USA (1989) 86, 2742–2746.
11. Lerman, L. S., Silverstein, K. Computational simulation of DNA melting and its application to denaturing gradient gel electrophoresis. Methods in Enzymol. (1987) 155, 482–501.
12. Kimmel, A. R., Berger, S. L. Preparation of cDNA and the generation of cDNA libraries : Overview. Methods in Enzymol. (1987) 152, 307–316.
13. Newton, C. R., Graham, A., Heptinstall, L. E., Powell, S. J., Summers, C., Kalsheker, N., Smith, J. C., Markham, A. F. Analysis of any point mutation in DNA. The amplification refractory mutation system (ARMS). Nucl.Acids Res. (1989) 17, 2503–2516.
14. Maruyama, K., Sugano, S. Oligo-capping: a simple method to replace the cap structure of eukaryotic mRNAs with oligoribonucleotides. Gene (1994) 138, 171–174.
15. Orita, M., Iwahana, H., Kanazawa, H., Hayashi, K., Sekiya, T. Detection of polymorphism of human DNA by gel electrophoresis as single-strand conformation polymorphisms. Proc.Natl.Acad.Sci.USA (1989) 86, 2766–2770.
16. Hatada, I., Hayashizaki, Y., Hirotsune, S., Komatsubara, H., Mukai, T. A genomic scanning method for higher organisms using restriction sites as landmarks. Proc.Natl.Acad.Sci.USA (1991) 88, 9523–9527.
17. Chomczynski, P., Sacchi, N. Single-step method of RNA isolation by acid guanidinium thiocyanate-phenol-chloroform extraction. Anal.Biochem. (1987) 162, 156–159.
18. Belyavsky, A. V., Vinogradova, T. V., Rajewsky, K. PCR-based cDNA library construction: General cDNA libaries at the level of a few cells. Nucl. Acids Res. (1989) 17, 2919–2932.
19. Sambrook, J., Fritsch, E. F., Maniatis, T., eds. Molecular Cloning. A laboratory manual. Second ed. (1989) Cold Spring Harbor Laboratory Press, New York.

---

We claim:

1. A method of identifying differential expression of messenger RNA (mRNA) among two or more different sources, comprising;

(a) obtaining mRNA samples from two or more sources;

(b) synthesizing a set of double stranded complementary DNA (cDNA) from each of the mRNA samples;

(c) generating a set of cDNA fragments for each sample by cleaving the sets of cDNA with at least one restriction endonuclease;

(d) separating cDNA fragments obtained through step (c) by gel electrophoresis;

(e) obtaining pictures of the separated cDNA fragments;

(f) comparing pictures of separated cDNA fragments; and (g) identifying specific cDNA fragments exhibiting different signal intensities in the pictures of separated cDNA fragments, wherein differential signal intensity of the cDNA fragments is indicative of differential expression of mRNA species among the sources.

2. A method according to claim 1, wherein the generating step (c) further comprises selecting subsets of the generated cDNA fragments comprising cDNA fragments originating either from the 3' end regions or from the 5' end regions of mRNAs in the mRNA samples.

3. A method according to claim 2, wherein the selecting of subsets of cDNA fragments comprises selecting subsets comprising cDNA fragments originating from the 3' end regions of mRNAs in the mRNA samples.

4. A method according to claim 2, wherein the selecting of subsets of cDNA fragments comprises selecting subsets comprising cDNA fragments originating from the 5' end regions of mRNAs in the mRNA samples.

5. A method according to claim 2, further comprising labeling cDNA fragments by introducing at one end of the cDNA fragments a detectable label selected from the group consisting of a radioactive label, a chemical group, and a specific sequence of nucleotides.

6. A method according to claim 5, wherein the selecting of the subsets of cDNA fragments comprises specifically immobilizing on a solid carrier the cDNA fragments originating either from the 3' or the 5' end regions of the mRNAs.

7. A method according to claim 6, wherein the selecting of the subsets of cDNA fragments further comprises:

ligating a double-stranded adaptor sequence or a single-stranded oligonucleotide to the immobilized cDNA fragments originating either from the 3' or the 5' end regions of the mRNAs, and reamplifying the immobilized cDNA fragments by a polymerase chain reaction.

8. A method according to claim 7, further comprising:

equalizing the degree of representation of different sequences within the subsets of cDNA fragments by removing highly represented sequences in one or more of the subsets of cDNA fragments by hybridizing nonimmobilized cDNA fragments with complementary strands immobilized on a solid carrier.

9. A method according to claim 7, further comprising:

dividing each subset of cDNA fragments into nonintersecting groups of cDNA fragments.

10. A method according to claim 9, wherein the dividing of each subset of cDNA fragments into nonintersecting groups of cDNA fragments comprises:

immobilizing labeled cDNA fragments in each subset of cDNA fragments on a solid phase, and, for each of a plurality of restriction endonucleases, i) cleaving the immobilized labeled cDNA fragments with a restriction endonuclease, and ii) collecting a group of cDNA fragments released by the cleaving with the restriction endonuclease.

11. A method according to claim 9, wherein the dividing of each subset of cDNA fragments into groups of cDNA fragments comprises performing a plurality of separate amplification reactions each using one of a plurality of combinations of paired primers which hybridize to end sequences common to all of the cDNA fragments, but wherein each primer in each pair of primers further contains an additional base contiguous with its 3' end.

12. A method according to claim 5, wherein the detectable label comprises a nucleotide labeled with $^{32}P$ or $^{33}P$.

13. A method according to claim 5, wherein the detectable label is a chemical group, and where the method further comprises:

transferring the separated cDNA fragments to a membrane, and detecting the separated cDNA fragments by:

contacting the separated cDNA fragments with a reagent that specifically binds the chemical group and is conjugated with an enzyme, and determining enzymatic activity of the enzyme.

14. A method according to claim 7, further comprising:

transferring the separated cDNA fragments to a membrane, and visualizing transferred cDNA fragments by hybridizing the fragments with a labeled oligonucleotide capable of hybridizing to an end sequence of the adaptor sequence.

15. A method according to claim 7, further comprising:

transferring the separated cDNA fragments to a membrane, and visualizing transferred cDNA fragments by hybridizing the fragments with a set of labeled oligonucleotides that are each complementary to an end sequence of the adaptor sequence but further comprise at least one additional base contiguous with their 3' ends.

16. A method according to claim 7, wherein the separating comprises separating the cDNA fragments by two-dimensional gel electrophoresis.

17. A method according to claim 16, wherein the separating comprises separating the cDNA fragments by length along a first dimension of the two-dimensional electrophoresis, and according to melting profile using a denaturing gradient along a second dimension of the two-dimensional electrophoresis.

18. A method according to claim 16, wherein the separating comprises separating single-chain cDNA fragments by length under denaturing conditions along a first dimension of the two-dimensional electrophoresis, and according to secondary structure in nondenaturing conditions along a second dimension of the two-dimensional electrophoresis.

19. A method according to claim 16, wherein the separating comprises:

separating the cDNA fragments according to length in along a first dimension of the two-dimensional electrophoresis, specifically cleaving the cDNA fragments in the gel by a set of at least two restriction endonucleases to provide cleaved cDNA fragments, and separating the cleaved cDNA fragments according to length along a second dimension of the two-dimensional electrophoresis.

20. A method of cloning of differentially expressed mRNAs, comprising:

(a) obtaining mRNA samples from different types of cells;

(b) synthesizing sets of double stranded complementary DNAs (cDNAs) from the mRNA samples;

(c) cleaving the sets of cDNAs with a restriction endonuclease to generate sets of cDNA fragments;

(d) selecting subsets of cDNA fragments comprising cDNA fragments originating either from the 3' end regions or from the 5' end regions of the mRNAs;

(e) separating the selected subsets of cDNA fragments in gels by electrophoresis;

(f) obtaining pictures of the separated cDNA fragments in the gels;

(g) comparing the pictures of the separated cDNA fragments to identify specific cDNA fragments exhibiting different signal intensities in the pictures of separated cDNA segments;

(h) extracting from one or more gels specific cDNA fragments exhibiting different signal intensities in different separation pictures;

(i) amplifying extracted cDNA fragments using a polymerase chain reaction to provide amplified cDNA fragments; and (j) cloning amplified cDNA fragments into a plasmid or phage vector.

21. A method of identifying differential expression among samples of messenger RNA (mRNA) by analyzing cDNA synthesized from the mRNA samples, comprising the steps of:

(a) generating a set of cDNA fragments from each mRNA sample by cleaving the synthesized cDNA with at least one restriction endonuclease;

(b) separating each set of cDNA fragments by gel electrophoresis;

(c) obtaining pictures of each set of separated cDNA fragments;

(d) comparing the pictures of the sets of separated cDNA fragments; and (e) identifying specific cDNA fragments exhibiting different signal intensities in the pictures of the sets of separated cDNA fragments, wherein a differential signal intensity is indicative of differential expression of mRNA.

22. A method of identifying differential expression among samples of messenger RNA (mRNA) by analyzing cDNA synthesized from the mRNA samples, comprising the steps of:

(a) generating a set of cDNA fragments from each mRNA sample by cleaving the synthesized cDNA with at least one restriction endonuclease;

(b) separating each set of cDNA fragments by gel electrophoresis;

(c) determining the gel coordinates and signal intensities of the separated cDNA fragments for each set; and (d) identifying specific cDNA fragments exhibiting different signal intensities in step (c), wherein a differential signal intensity is indicative of differential expression of mRNA.

23. A method of identifying differential expression of a sample of messenger RNA (mRNA) by analyzing cDNA synthesized from the mRNA sample, comprising the steps of:

(a) generating a set of cDNA fragments from the mRNA sample by cleaving the synthesized cDNA with at least one restriction endonuclease;

(b) separating the set of cDNA fragments by gel electrophoresis;

(c) determining the gel coordinates and signal intensities of the separated cDNA fragments;

(d) comparing the gel coordinates and signal intensities from step (c) to a database of gel coordinates and signal intensities for cDNA fragments prepared from another sample; and (e) identifying specific cDNA fragments exhibiting different signal intensities in step (d), wherein a differential signal intensity is indicative of differential expression of mRNA.

24. A method of identifying differential expression of messenger RNA (mRNA) among a first source and a second source, comprising:

(a) obtaining an mRNA sample from the first source;

(b) synthesizing a set of double stranded complementary DNA (cDNA) from the mRNA sample;

(c) generating a set of cDNA fragments from the mRNA sample by cleaving the set of cDNA with at least one restriction endonuclease;

(d) separating the set of cDNA fragments by gel electrophoresis;

(e) obtaining a picture of the separated cDNA fragments and determining gel coordinates and signal intensities of the cDNA fragments;

(f) comparing the gel coordinates and signal intensities in step (e) with a database of gel coordinates and signal intensities for cDNA fragments prepared from the mRNA sample from the second source; and (g) identifying specific cDNA fragments exhibiting different signal intensities, wherein a differential signal intensity is indicative of differential expression of mRNA.

25. A method according to any one of claims 21–24, wherein the identification of differential expression involves a comparison of mRNA selected from the groups of cells consisting of (a) different cell types and (b) the same type of cell.

26. A method according claim 25, wherein said cDNA fragments comprise a detectable label.

27. A method according to claim 26, wherein said detectable label is selected from the group consisting of a radioactive label, a chemical group and a specific sequence of nucleotides.

28. A method according to claim 27, wherein said detectable label comprises a nucleotide labeled with $^{32}P$ or $^{33}P$.

29. A method according to claim 26, wherein said detectable label permits non-radioactive detection of said cDNA fragments.

30. A method according to claim 29, wherein said non-radioactive detection is by chemiluminescent detection.

31. A method according to claim 25, wherein said cDNA fragments are divided into non-intersecting subsets.

32. A method according to claim 25, wherein said cDNA fragments are selected from the group consisting of: (a) the 5' end of said mRNAs; and (b) the 3' end of said mRNAs.

33. A method according to claim 32, wherein said subsets are selected by specifically immobilizing on a solid carrier the cDNA fragments originating from either the 3' or 5' end regions of the mRNAs.

34. A method according to any one of claim 21–24, wherein the step of generating cDNA fragments further comprises ligating an adaptor sequence to the cDNA fragments following restriction endonuclease cleavage, wherein said adaptor sequence is complementary to the restriction endonuclease cleavage site.

35. A method according to any one of claims 21–24, further comprising reducing the degree of representation of highly represented sequences among said cDNA fragments by hybridizing non-immobilized cDNA fragments with complementary strands immobilized on a solid carrier.

36. A method according to claim 35, wherein the method further comprises:

labeling the cDNA fragments with a detectable chemical group label;

transferring the separated cDNA fragments to a membrane; and detecting the separated cDNA fragments by contacting the separated cDNA fragments with a reagent the specifically binds the chemical group and that is conjugated with an enzyme, and detecting the presence of the enzyme.

37. A method according to claim 35, further comprising:

labeling the cDNA fragments with a detectable oligonucleotide label;

transferring the separated cDNA fragments to a membrane; and detecting transferred cDNA fragments by hybridizing the fragments with a labeled oligonucleotide capable.

38. A method according to any one of claims 21–24, wherein the gel electrophoresis is two-dimensional electrophoresis.

39. A method according to claim 38 wherein said cDNA fragments are separated by length along a first dimension and according to melting profile using a denaturing gradient along a second dimension.

40. A method according to claim 38, wherein said cDNA fragments are separated by length under denaturing conditions along a first dimension and according to secondary structure under non-denaturing conditions along a second dimension.

41. A method according to claim 38, wherein said cDNA fragments are:

separated according to length along a first dimension;

cleaved in the gel by a set of at least two restriction endonucleases to provide cleaved cDNA fragments; and separated according to length along a second dimension.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 22 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:1:

G G G A G G C C C T   T T T T T T T T T   T T        2 2

( 2 ) INFORMATION FOR SEQ ID NO:2:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:2:

AAGGAATTCC CCCCCCCCC C        21

( 2 ) INFORMATION FOR SEQ ID NO:3:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:3:

GATCGTTTTT TGAAGCTTGG AGCCCAC        27

( 2 ) INFORMATION FOR SEQ ID NO:4:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:4:

GTGGGCTCCA AGCTTCAAAA AAC        23

( 2 ) INFORMATION FOR SEQ ID NO:5:

( i ) SEQUENCE CHARACTERISTICS:
        ( A ) LENGTH: 16 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:5:

GTGGGCTCCA AGCTTC        16